US00PP09801P

United States Patent [19]

Stemkens

[11] Patent Number: Plant 9,801

[45] Date of Patent: Feb. 11, 1997

[54] GERANIUM PLANT NAMED 'SANBLOTCH'

[75] Inventor: Henricus G. W. Stemkens, Hoorn, Netherlands

[73] Assignee: S&G Seeds B.V., Enkhuizen, Netherlands

[21] Appl. No.: 572,560

[22] Filed: Dec. 14, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 3,888 5/1976 Duffett et al. ..... Plt./87.12

*Primary Examiner*—Howard J. Locker

*Attorney, Agent, or Firm*—Lynn Marcus-Wyner

[57] ABSTRACT

A new ivy-leaved geranium particularly distinguished by its well-branched shape and compact growth, early appearing deep lilac with blotch single flowers with low seedset, good precocity and floral richness.

1 Drawing Sheet

BACKGROUND OF THE NEW PLANT

The present invention comprises a new distinct cultivar of ivy-leaved geranium, botanically known as *Pelargonium peltatum* hybrid. The new cultivar is propagated from cuttings resulting from the cross of L218 and P174. L218 is a lilac flowering peltatum having no pollen. L218 is not commercially available and is not known by any synonyms. P174 is a red lilac with blotch colored peltatum, with good growth and having pollen. P174 is not commercially available and is not known by any synonyms. Neither L218 or P174 have been patented. As a result of this cross the present cultivar was created in 1991 in Enkhuizen, Netherlands and has been repeatedly asexually reproduced by cuttings in Enkhuizen, Netherlands and Stuttgart, Germany over a three year period. It has been found to retain its distinctive characteristics through successive propagations, and this novelty appears to be firmly fixed.

DESCRIPTION OF THE DRAWING

This new geranium plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics were collected from asexual reproductions carried out in Enkhuizen, Netherlands. The plant history was taken on 12 week old plants, blossomed under natural light in a greenhouse. Color readings were taken in the greenhouse under ambient light. Color references are primarily to The RHS Color Chart of the Royal Horticultural Society of London.

The Plant

Classification:

*Botanical.*—*Pelargonium peltatum* — Hybrid.

*Commercial.*—Ivy-leaved geranium.

Parentage:

*Female parent.*—A seedling named L218 is one of our seedlings from our L-generation of plants bred in 1986.

*Pollen parent.*—A seedling named P174 is one of our seedlings from our P-generation of plants bred in 1988.

Form: Very compact, hanging.

Shape: Round.

Stalk length: About 170–220 mm in April and 430–510 mm in September.

Number of stems per stalk: Approximately 4–8 from may until the end of September.

Number of stalks per plant: Approximately 5–7 in October.

Internode length: About 40–65 mm depending on the light where the plant is propagated.

Growth rate: Hanging and vigorous.

Strength: Very good.

Branching character: Good branching.

Foliage:

*Quantity.*—Many robust leaves.

*Size.*—Small, from 45–58 mm.

*Shape.*—5 lobed, peltate.

*Texture.*—Hairy at young leaf stage (1 cm long), becoming smoother with increased maturity.

*Zonation.*—Almost circular band 2–4 mm. thick, light brown, diameter about 10 mm.

Ribs and Veins: 5 Ribs.

Color:

*Upper side.*—Medium green 141A.

*Lower side.*—Light green 143A.

Length of leaf stem: 25–40 mm.

The Bud

Peduncle length: 110–155 mm, depending on the season.

Size:

*Diameter.*—2–3 mm.

*Length.*—9 mm.

Shape: Elliptical.

Form: Ovoid and pointed.

Rate of opening: Medium.

Color:

*When sepals first divide.*—137D.

*When petals begin to unfurl.*—138A.

Sepals:

*Color.*—Inside — 138B. Outside — 138A.

*Form.*—Standing up.

Pedical:

*Length.*—About 25–30 mm.

*Strength.*—Very strong, the florets are arranged asymmetric around the middle of the cluster. The florets are approximately 35 mm in diameter.

*Color.*—Mature: one side 138A, other side 176A.

The Flower

Blooming habit: Continuous and profusely from April until October.
Size: About 70–90 mm.
Borne: In a cluster having between 4–7 flowers per cluster.
Form: Horizontal symmetric, quite open. When the flowers mature, the petals curl back.
Petals:
*Numbers.*—5 per floret, between 80–100 clusters in one season per plant.
*Arrangement.*—2 upper petals, longer and broader, more curled back. 3 lower petals, smaller.
*Form.*—Upper obcordate.
*Color.*—Outer petal — 78B, light purple. Inside petal — white (lower) or red purple (upper).
*Markings.*—See pattern.
*Reverse side.*—Light purple 78D.
*Pattern.*—The upper two petals have two long red purple margins (colour 71A) which fade into the veins. Between the end of the two lines there is a big red purple blotch (color 67A). Under this blotch there is a long section of white pink. The reverse side has the same stripes, but lighter in colour. The lower petals have very small (2 mm) pink lines, mostly 2. The outer parts of the petals are purple colored (78C), in the middle lighter.
*Texture.*—Smooth.
*Appearance.*—Satiny.
Petals remain on stem about 5–7 days depending on the weather.
Persistence: Petals drop, so no picking of matured clusters necessary.
Disease resistance: Sanblotch does not suffer from Botrytis.
Weather resistance: Sanblotch is not unusually affected by wet or hot weather.
Lasting quality:
*On the living plant in pot.*—About 10–14 days.
*As a cut flower.*—About 5 days.
Fragrance: No perceptible fragrance.

Reproductive Organs

Stamens:
*Anthers.*—Either none or totally shriveled. When present, are yellow in color.
*Filaments.*—Usually 7, about 1 mm in length, and white in color.
Pollen: If available, then yellow in color.
Pistils:
*Number.*—One.
*Length.*—Appr. 6 mm.
*Stigmas.*—Pink in color, divided in 5 papillae.
Ovaries: Green in color.
Seed: Non fertile.

What is claimed is:

1. A new and distinct cultivar of ivy-leaved geranium plant substantially as herein shown and described, particularly distinguished by its very short internodes and well branched plant, and its early appearing red lilac with blotch single flowers which set little seed.

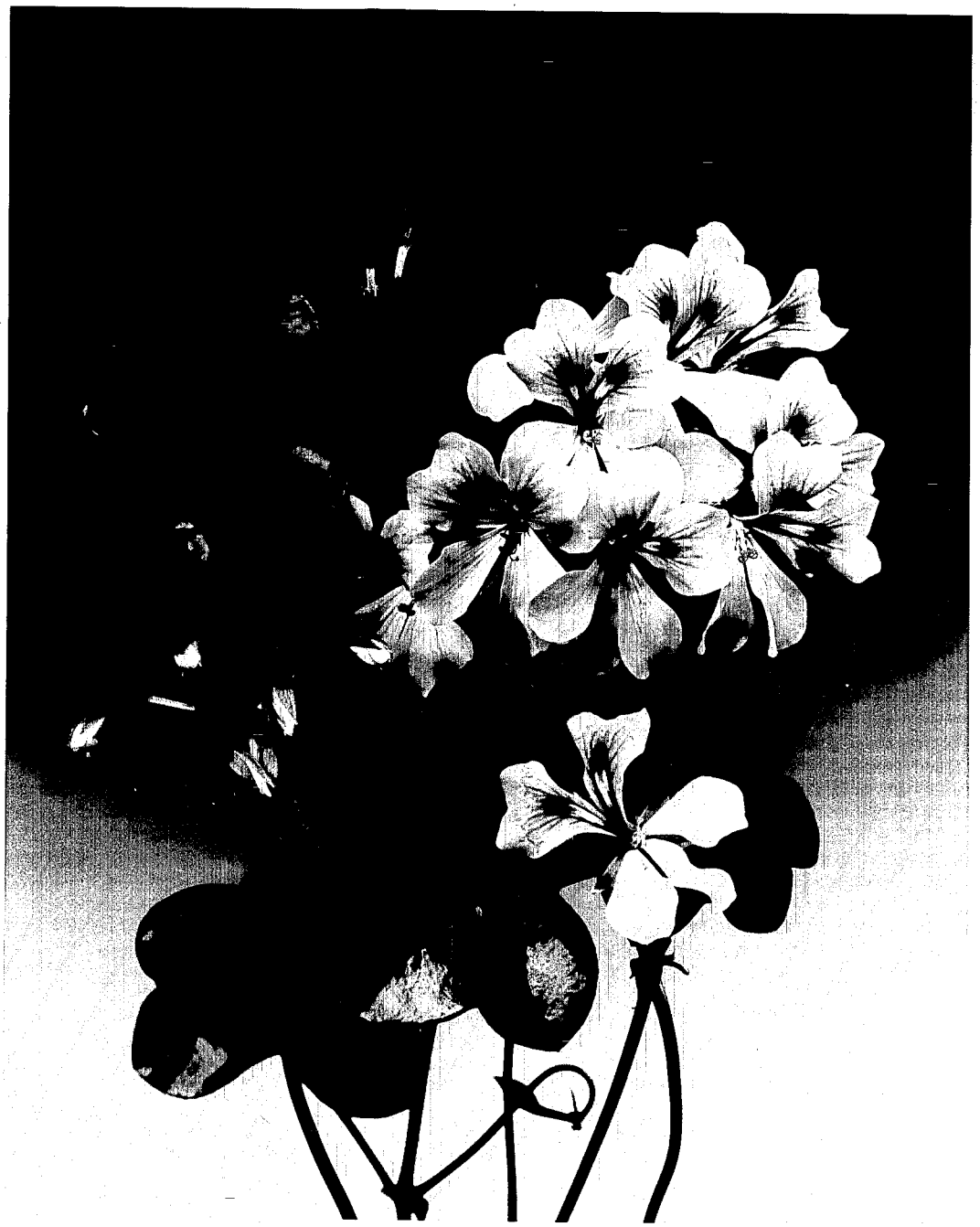

* * * * *